United States Patent
Kontur et al.

(10) Patent No.: US 9,017,402 B2
(45) Date of Patent: Apr. 28, 2015

(54) INTRAOCULAR IMPLANT

(75) Inventors: Laszlo Kontur, Munich (DE); Nandor Turkevi-Nagy, Zsambek (HU); Gilles Bos, Plan-les-Ouates (CH)

(73) Assignee: Medicontur Orvostechnikai Korlatolt Felelossegu Tarsasag, Zsambek (HU)

( * ) Notice: Subject to any disclaimer, the term of this patent is extended or adjusted under 35 U.S.C. 154(b) by 0 days.

(21) Appl. No.: 13/395,479

(22) PCT Filed: Sep. 10, 2010

(86) PCT No.: PCT/EP2010/063292
§ 371 (c)(1),
(2), (4) Date: Apr. 25, 2012

(87) PCT Pub. No.: WO2011/029897
PCT Pub. Date: Mar. 17, 2011

(65) Prior Publication Data
US 2012/0203337 A1  Aug. 9, 2012

(30) Foreign Application Priority Data
Sep. 11, 2009 (FR) ..................................... 09 04353

(51) Int. Cl.
*A61F 2/16* (2006.01)

(52) U.S. Cl.
CPC ....... *A61F 2/1613* (2013.01); *A61F 2002/1681* (2013.01)

(58) Field of Classification Search
USPC ............................................. 623/6.38–6.54
See application file for complete search history.

(56) References Cited

U.S. PATENT DOCUMENTS

| | | | | |
|---|---|---|---|---|
| 5,571,177 | A * | 11/1996 | Deacon et al. | 623/6.47 |
| 6,179,870 | B1 | 1/2001 | Sourdille et al. | |
| 6,554,860 | B2 * | 4/2003 | Hoffmann et al. | 623/6.43 |
| 6,926,744 | B1 * | 8/2005 | Bos et al. | 623/6.11 |
| 7,569,073 | B2 * | 8/2009 | Vaudant et al. | 623/6.17 |
| 2003/0204257 | A1 * | 10/2003 | Southard | 623/6.46 |
| 2006/0276892 | A1 * | 12/2006 | Toop | 623/6.16 |
| 2008/0109077 | A1 | 5/2008 | Bos | |

FOREIGN PATENT DOCUMENTS

| | | |
|---|---|---|
| DE | 102 02 679 | 8/2003 |
| EP | 0 897 294 | 11/2001 |
| FR | 2 790 661 | 9/2000 |
| FR | 2 868 286 | 10/2005 |
| WO | 01/03610 | 1/2001 |
| WO | 2004/010895 | 2/2004 |
| WO | 2005/099631 | 10/2005 |

OTHER PUBLICATIONS

International Search Report dated Oct. 1, 2010, corresponding to PCT/EP2010/063292.

* cited by examiner

*Primary Examiner* — Paul Prebilic
(74) *Attorney, Agent, or Firm* — Young & Thompson

(57) ABSTRACT

An intraocular implant (1) including an optical portion (2) and a haptic portion (3), the haptic portion including two diametrically opposite haptic systems (3a, 3b), characterized in that each of the haptic systems (3a, 3b) includes two substantially identical haptics (4, 5) interconnected by their respective distal ends (4a, 5a), the respective proximal ends (4b, 5b) of the two haptics (4, 5) being connected to the optical portion (2) via a stalk (6), the width of each of the haptics (4, 5) decreasing continuously all along the haptic toward the distal end (4a, 5a).

11 Claims, 3 Drawing Sheets

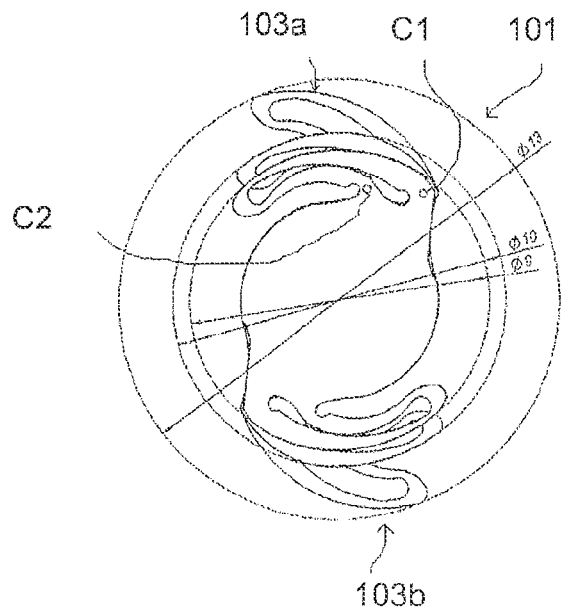
FIG. 3
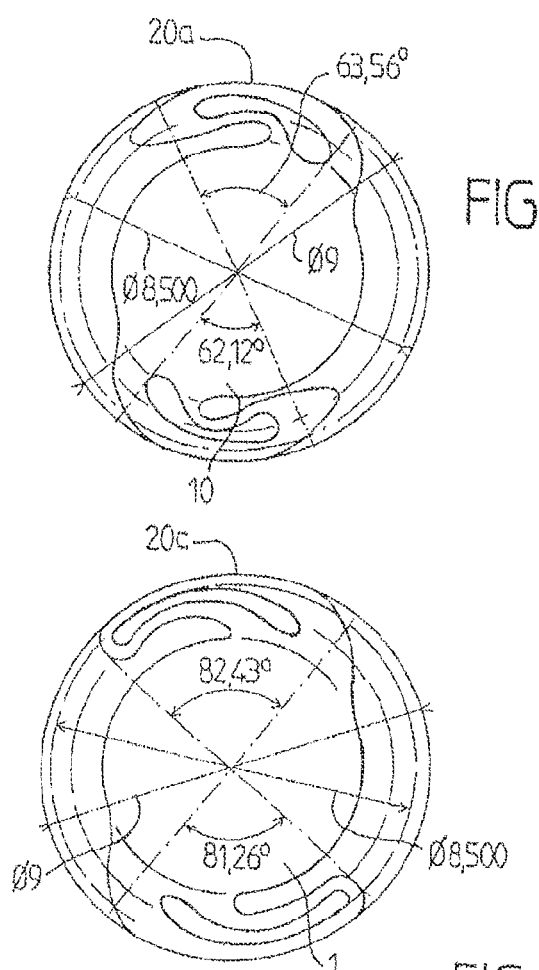
FIG.4a
FIG.4c
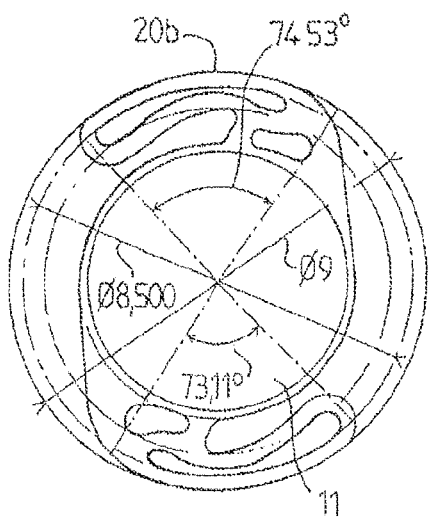
FIG.4b
(PRIOR ART)

INTRAOCULAR IMPLANT

The present invention concerns an intraocular implant, for example an intraocular lens.

An intraocular implant includes an optical portion, forming the corrector optical system proper, and a haptic portion, which is used to fit and fix the optical portion inside the eye in the appropriate position.

Such an implant is generally produced in a flexible material enabling it to be folded or rolled, so as to be able to insert it into the eye via a small incision, the implant resuming its normal shape and dimensions when it is placed in the eye.

Numerous intraocular implants have been proposed over the last two decades to improve their implantation following extraction of the crystalline lens, notably in the case of cataracts.

The objective is to obtain an optimum position of the implant in the eye, and notably in the lens capsule, in order to limit the formation of creases in the capsule. Limiting the formation of creases in the capsule has the effect of limiting the migration of cells and thus posterior capsule opacification (PCO).

A reference method for measuring the contact between an implant (and notably the haptics of the haptic portion of the implant) and a lens capsule is described in the standard EN ISO 11979-3 section 4.8 Angle of contact (p.3). This standard covers checking various parameters characteristic of 11 mm and 10 mm implants. These two theoretical diameters were chosen statistically to correspond to that of the ciliary sulcus and the lens capsule.

However, these diameters are currently being called into question. Clinical research showed that the lens capsule shrank in the months following implantation to a diameter substantially less than 10 mm, probably closer to 9 mm, and that the final shape of the lens capsule was more oval than circular. The major axis of the oval coincides with the axis along which the lens capsule is tensioned by the haptics of the haptic portion of the implant. One way to simulate the final deformation of a lens capsule subject to the traction stress of the haptics is to use a flexible ring having an initial inside diameter close to 9 mm and to insert an intraocular implant therein.

The intraocular implant described in patent application EP 0 897 294 includes a haptic portion comprising a main haptic and a secondary haptic, notably thinner than the main haptic, which connects the distal end of the main haptic to the optical portion. The width of each haptic is substantially constant throughout its length.

The intraocular implant described in the patent application FR 2 868 286 includes a haptic portion forming a loop of substantially constant width that is attached to the optical portion via a stalk.

The intraocular implants described in the above two documents enable good positioning of the implant in a circular lens capsule, but positioning problems are encountered if the lens capsule has an oval shape.

An object of the present invention is to propose an intraocular implant that avoids the aforementioned problems and enables optimum positioning of the implant in an oval lens capsule.

To this end, the invention provides an intraocular implant including an optical portion and a haptic portion, the haptic portion comprising two diametrically opposite haptic systems, characterized in that each of said haptic systems comprises two substantially identical haptics interconnected by their respective distal ends, the respective proximal ends of said two haptics being connected to said optical portion via a stalk, the width of each of said haptics decreasing continuously all along the haptic toward said distal end.

The decrease in the width of each of said haptics is preferably substantially proportional to the distance from the proximal end of said haptic.

In one embodiment of the invention said decrease is in the range −30% to −60%, preferably −40% to −50%, the width of said haptics being in the range 0.70 mm to 0.30 mm in their proximal portion, preferably 0.50 mm to 0.35 mm, the width of said haptics (4, 5) being in the range 0.3 mm to 0.15 mm in their distal portion, preferably of the order of 0.18 mm.

Each of said two haptics advantageously includes, in the vicinity of its proximal end, a widthwise attenuation.

Said attenuation advantageously constitutes a localized reduction of the width of the haptic of the order of −15% to −40%, and preferably −20% to −35%, the smallest width of the haptic at the location of this reduction being in the range 0.20 mm to 0.50 mm, and preferably 0.25 mm to 0.40 mm.

In one embodiment of the invention said attenuation is produced by a notch.

The invention will be better understood, and other objects, details, features and advantages thereof will become more clearly apparent in the course of the following detailed explanatory description of embodiments of the invention given by way of purely illustrative and nonlimiting example and with reference to the appended diagrammatic drawings.

In the drawings:

FIG. 3 is a view similar to FIG. 2 showing a number of positions of the haptic systems of the intraocular lens of the second embodiment of the invention;

FIGS. 4a to 4c respectively show two prior art lenses and a lens of the first embodiment of the invention each in place in a circular lens capsule; and FIGS. 5a to 5d respectively show two prior art lenses, a lens of the first embodiment of the invention and a lens of the second embodiment of the invention each in place in a ring.

Figure 1:
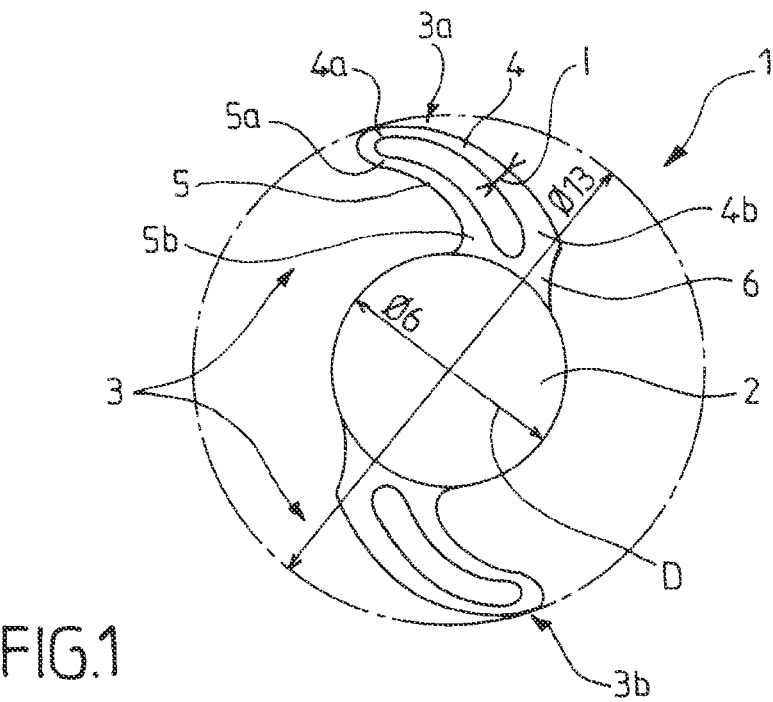
FIG. 1 is a simplified diagrammatic view from above of an intraocular lens of a first embodiment of the invention.

FIG. 1 shows a one-piece flexible intraocular lens 1 of a first embodiment of the invention. The lens 1 is adapted to be implanted in the lens capsule of an eye, in a manner known in itself.

The intraocular lens 1 includes an optical portion 2 and a haptic portion 3. The optical portion 2 is substantially circular and its diameter D is approximately equal to 6 mm, for example.

The haptic portion 3 comprises two diametrically opposite haptic systems 3a and 3b. The two haptic systems 3a, 3b being identical, only the haptic system 3a is described in detail hereinafter.

The haptic system 3a comprises two substantially identical haptics 4 and 5 interconnected by their distal ends 4a and 5a. The respective proximal ends 4b and 5b of the haptics 4, 5 are connected to the optical portion 2 via a stalk 6.

The width 1 of each haptic 4, 5 decreases continuously all along the haptic 4, 5, the decrease being substantially proportional to the distance from the proximal end 4b, 5b of the haptic 4, 5. By the width of the haptic 4, 5 is meant the transverse dimension of the haptic 4, 5 in the plane of the figures. The reduction proportional to distance means that the reduction of the width 1 of each haptic 4, 5 is regular and homogeneous throughout the length of the haptic 4, 5. The reduction is in the range −30% to −60%, for example, preferably −40% to −50%. The width of the haptics 4, 5 is in the range 0.70 mm to 0.30 mm in their proximal portion, preferably in the range 0.50 mm to 0.35 mm. The width of the haptics 4, 5 is in the range 0.3 mm to 0.15 mm in their distal portion, the width being preferably of the order of 0.18 mm.

The two haptics 4, 5 cooperate, producing a greater force to resist flexing with haptics 4, 5 of small width and thickness compared to an intraocular lens with only one haptic.

The lens 1 also has advantages for implantation, because the presence of two similar haptics 4, 5 enables a great capacity for deformation to be preserved, which facilitates injection with the aid of an injector and a cartridge compared to a lens having only one haptic.

FIG. 4a shows a lens 10 as described in the document EP 0 897 294, which is placed in a 9 mm diameter circular lens capsule 20a. FIG. 4b shows a lens 11 as described in the document FR 2 868 286 which is placed in a circular lens capsule 20b identical to the capsule 20a. FIG. 4c shows the lens 1 of the invention placed in a circular lens capsule 20c identical to the capsule 20a. Measurements carried out in accordance with the standard yield an angle of contact of 63.56° for the lens 10, 74.53° for the lens 11, and 82.43° for the lens 1. The quality of the positioning of these three lenses 10, 11, 1 in circular lens capsules 20a, 20b, 20c is therefore substantially similar.

Figure 5A:
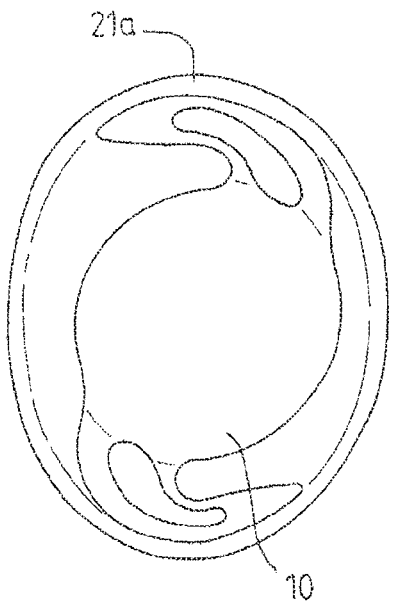
Figure 5B:
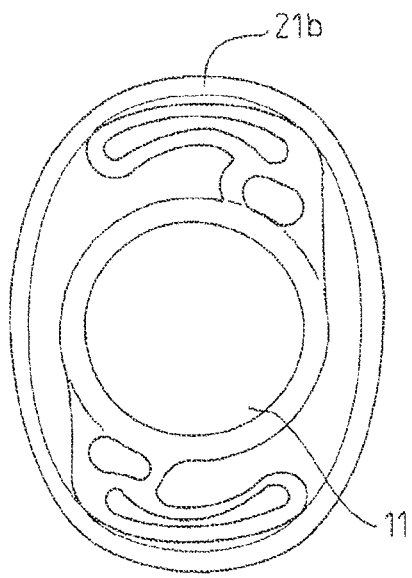
Figure 5C:
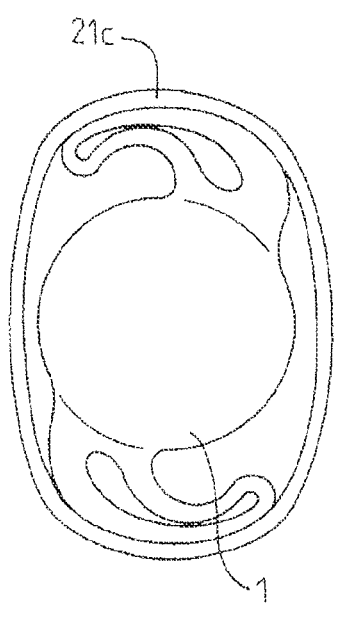

FIG. 5a shows the lens 10, which is placed in a flexible ring 21a adapted to be deformed in oval fashion by the effect of the tension of the haptics. FIG. 5b shows the lens 11, which is placed in a ring 21b identical to the ring 21a. FIG. 5c shows the lens 1, which is placed in a ring 21c identical to the ring 21a. It is seen in FIG. 5a that there is a large gap between the haptic portion and the ring at the level of the rear of the main haptic. It is also seen that the lens 10 is not perfectly centered in the ring 21a, despite repeated manipulation by the operator attempting to place it at the center of this ring deformed in non-symmetrical fashion. FIG. 5b shows that there is an interruption in the bearing engagement at the level of the center of the loop. Such an interruption transforms the long bearing engagement seen in FIG. 4b, measured at approximately 74°, with two localized bearing engagements at the ends of each of the two loops. In contrast, FIG. 5c shows that the haptic 4 is in contact with the ring 21c over all its length. The area of contact is therefore much greater for the lens 1. The lens 1 is perfectly centered in a ring deformed in relatively symmetrical fashion relative to the optical axis. Consequently, the lens 1 enables better positioning to be achieved.

Figure 2:
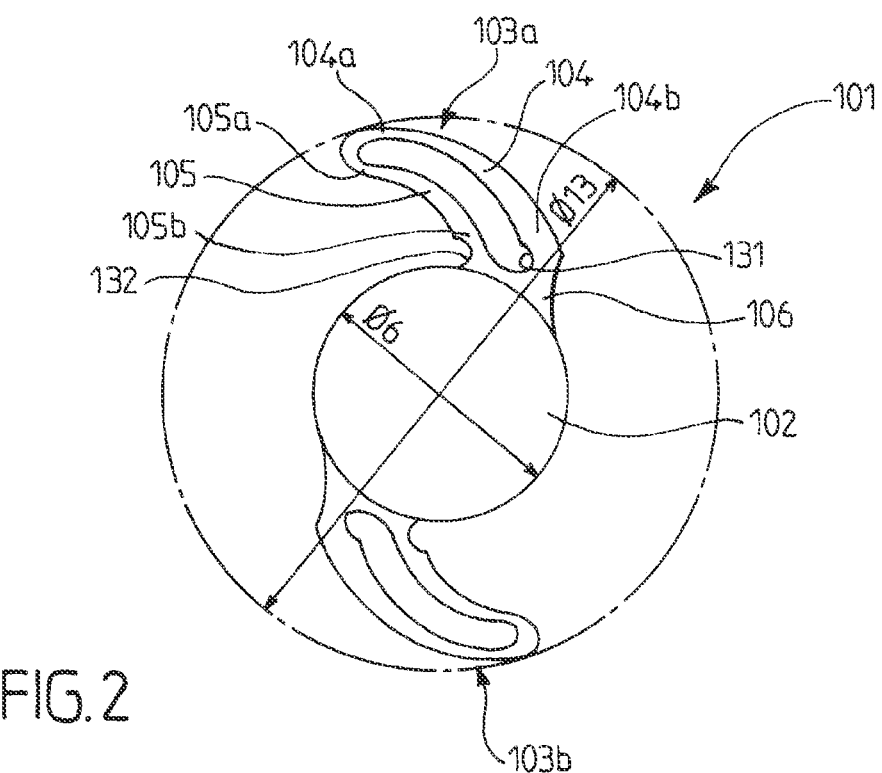
FIG. 2 is a view similar to FIG. 1 showing an intraocular lens of a second embodiment of the invention.

FIGS. 2 and 3 show a lens 101 of a second embodiment of the invention. Here each haptic 104, 105 includes, in the vicinity of its proximal end 104b, 105b, a widthwise attenuation 131, 132. In the figures, the attenuation 131, 132 is produced by a notch cut locally in the width of the haptic 104, 105. The attenuation 131, 132 constitutes a localized reduction of the width of the haptic 104, 105 of the order of −15% to −40%, and preferably −20% to −35%, the smallest width of the haptic 104, 105 at the location of this reduction being in the range 0.20 mm to 0.50 mm, preferably 0.25 mm to 0.40 mm.

The attenuation 131, 132 enables a preferential point of flexing of the haptic 104, 105 to be produced. Consequently, the deformation of the haptic 104, 105 is composed of a global deformation of its curvature, accompanied by a rotation of the haptic 104, 105 about a point C1, C2 close to the attenuation 131, 132. In other words, the attenuation 131, 132 forms an instantaneous center of rotation C1, C2 of the haptic 104, 105. The attenuations 131, 132 of the two haptics 104, 105 of the haptic system 103a cooperate to form a double instantaneous center of rotation of the haptic system 103a, which leads to global deformation of the haptic system 103a comparable to that of a pantograph. FIG. 3 shows this deformation diagrammatically, showing three positions of the haptic systems 103a, 103b. The attenuations 131, 132 enable the stiffness transverse to the plane of deformation of the haptic system 103a to be increased, i.e. the attenuations 131, 132 prevent parasitic deformation in a plane perpendicular to the optical axis, which enables the risks of luxation to be limited. Such luxation would cause tilting of the optical portion 102 and would induce not only an optical aberration but also a risk of breaking of the contact between the posterior periphery of the optical portion 102, where the square edge intended to combat centripetal cellular proliferation, and the posterior capsule is located.

Figure 5D:
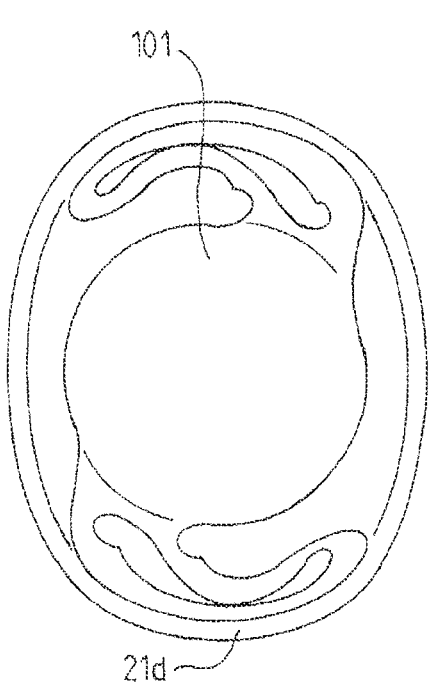

FIG. 5d shows the lens 101 placed in a ring 21d identical to the ring 21a. It is seen that the area of contact is substantially identical to the area of contact of the lens 1.

The lenses 1, 101 prevent the presence of localized contact of a haptic 4, 5, 104, 105 with the lens capsule, notably at the level of the distal end 4a, 5a, 104a, 105a of the haptic 4, 5, 104, 105. The effect of such localized contact is to cause creasing of the posterior capsule, deleterious to the contact between the capsule and the optical portion 2, 102, and may lead to the appearance of creases enabling colonization of the central posterior capsule by equatorial epithelial cells. The lens 101 also prevents serious reduction of the exterior curvature of the capsule, of the type seen at 22c in FIG. 5c.

The lenses 1, 101 are more effective at resisting tilting and luxation of the lens capsule, thus enabling intimate contact to be maintained between the optical portion 2, 102 and the posterior capsule over the whole of the periphery thereof.

Although the invention has been described in relation to a plurality of particular embodiments, it is obvious that it is not limited thereto and that it encompasses all technical equivalents of the means described together with their combinations that fall within the scope of the invention.

The invention claimed is:

1. An intraocular implant (101) comprising:
   an optical portion (102) forming a corrector optical system relative to an optical axis; and
   a haptic portion (103) that fits and fixes the optical portion inside an eye, the haptic portion comprising two diametrically opposite haptic systems (103a, 103b),
   wherein each of said haptic systems (103a, 103b) comprises two haptics (104, 105), each said haptic having a distal end (104a, 105a) and a proximal end (104b, 105b), said two haptics (104, 105) being interconnected by their respective distal ends (104a, 105a),
   wherein the respective proximal ends (104b, 105b) of said two haptics (104, 105) are connected to each other via a stalk and, via said stalk (106) to said optical portion,
   wherein each of said haptics includes, in a vicinity of the respective proximal end, a widthwise attenuation (131, 132) that respectively define a preferential point of flexing of each of said haptics, and
   wherein a width of each of said haptics (104, 105) decreases continuously along an entire length from an end of each widthwise attenuation to said distal end (104a, 105a) where said two haptics are interconnected by their respective distal ends, the width of each of said haptics being defined as the transverse dimension thereof in a plane that extends through said haptics and is perpendicular to the optical axis.

2. The intraocular implant as claimed in claim 1, wherein the decrease in the width of each of said haptics (104, 105) is proportional to a distance from the proximal end (104b, 105b) of said haptic.

3. The intraocular implant as claimed in claim 1, wherein each said widthwise attenuation constitutes a localized reduction of the width of the haptic of the order of −15% to −40%, a smallest width of the haptic at the location of this localized reduction being in the range 0.20 mm to 0.50 mm.

4. The intraocular implant as claimed in claim 1, wherein said widthwise attenuation (131, 132) is a notch.

5. An intraocular implant as claimed in claim 3, wherein said widthwise attenuation (131, 132) is a notch.

6. The intraocular implant as claimed in claim 1, wherein each said widthwise attenuation constitutes a localized reduction of the width of the haptic of the order of −20% to −35%, the smallest width of the haptic at the location of this localized reduction being in the range 0.25 mm to 0.40 mm.

7. The intraocular implant as claimed in claim 1, wherein each widthwise attenuation provides the preferential point of flexing of each haptic such that a deformation of each haptic is composed of a global deformation accompanied by a rotation of each haptic about an instantaneous center of point (C1, C2) of each haptic close to each widthwise attenuation, each widthwise attenuation of the haptics of each haptic system cooperating to form a double instantaneous center of rotation of each respective haptic system.

8. The intraocular implant as claimed in claim 1, wherein said widthwise attenuation constitutes a localized reduction of the width of the haptic of the order of −15% to −40%.

9. The intraocular implant as claimed in claim 1, wherein said attenuation constitutes a localized reduction of the width of the haptic of the order of −20% to −35%.

10. The intraocular implant as claimed in claim 1, wherein a smallest width of each said widthwise attenuation is in the range of 0.25 mm to 0.40 mm.

11. The intraocular implant as claimed in claim 1, wherein a smallest width of each said widthwise attenuation is in the range of 0.20 mm to 0.50 mm.

* * * * *